US007961324B2

(12) United States Patent
Okabayashi

(10) Patent No.: US 7,961,324 B2
(45) Date of Patent: Jun. 14, 2011

(54) WAVELENGTH IDENTIFICATION METHOD AND ANALYZER

(75) Inventor: Osamu Okabayashi, Mishima (JP)

(73) Assignee: Beckman Coulter, Inc., Brea, CA (US)

(*) Notice: Subject to any disclaimer, the term of this patent is extended or adjusted under 35 U.S.C. 154(b) by 53 days.

(21) Appl. No.: 12/500,908

(22) Filed: Jul. 10, 2009

(65) Prior Publication Data

US 2010/0007886 A1     Jan. 14, 2010

Related U.S. Application Data

(63) Continuation of application No. PCT/JP2007/072667, filed on Nov. 22, 2007.

(30) Foreign Application Priority Data

Jan. 12, 2007   (JP) ................................ 2007-004896

(51) Int. Cl.
   *G01N 21/00*   (2006.01)
(52) U.S. Cl. ........ 356/432; 356/436; 436/55; 422/82.09
(58) Field of Classification Search .......... 356/432–440, 356/244, 246, 300, 326, 319; 436/55, 164, 436/162; 422/82.05, 82.06, 82.07, 82.08, 422/82.09
See application file for complete search history.

(56) References Cited

U.S. PATENT DOCUMENTS

| 6,980,285 | B1  | 12/2005 | Hansen |
| 2004/0176922 | A1* | 9/2004 | Samsoondar .................... 702/86 |
| 2004/0185392 | A1* | 9/2004 | Suzuki et al. ................. 430/546 |
| 2006/0153738 | A1  | 7/2006 | Tanji |
| 2010/0099194 | A1* | 4/2010 | Okabayashi .................... 436/55 |

FOREIGN PATENT DOCUMENTS

| JP | 06-074823 | 3/1994 |
| JP | 2002-518670 | 6/2002 |
| JP | 2004-132706 | 4/2004 |
| JP | 2006-162355 | 6/2006 |

* cited by examiner

*Primary Examiner* — Hoa Q Pham
(74) *Attorney, Agent, or Firm* — Kilpatrick Townsend & Stockton LLP

(57) ABSTRACT

An analyzer analyzes a sample based on optical characteristics of the sample. The analyzer includes a measuring unit that measures absorbances of two or more wavelength identifying samples having different concentrations and having absorbance characteristics in which there is no extremum in a wavelength band including a wavelength to be identified, the wavelength identifying samples being made of a same material; a calculator that obtains a gradient of a straight line indicating a relationship between the concentrations and the absorbances of the identifying samples measured by the measuring unit; and an identifier that identifies an actual wavelength of light to be measured by the measuring unit, based on a degree of coincidence between the gradient of the straight line calculated by the calculator and at least one pre-obtained reference gradient of a straight line indicating a relationship between concentrations and absorbances of reference samples made of the same material as the wavelength identifying samples for at least one wavelength.

6 Claims, 5 Drawing Sheets

| WAVELENGTH [nm] | a | b |
|---|---|---|
| 570 | 2.9905 | 0.0298 |
| 571 | 2.8861 | 0.0260 |
| 572 | 2.7673 | 0.0230 |
| 573 | 2.6365 | 0.0203 |
| 574 | 2.4899 | 0.0175 |
| 575 | 2.3224 | 0.0158 |

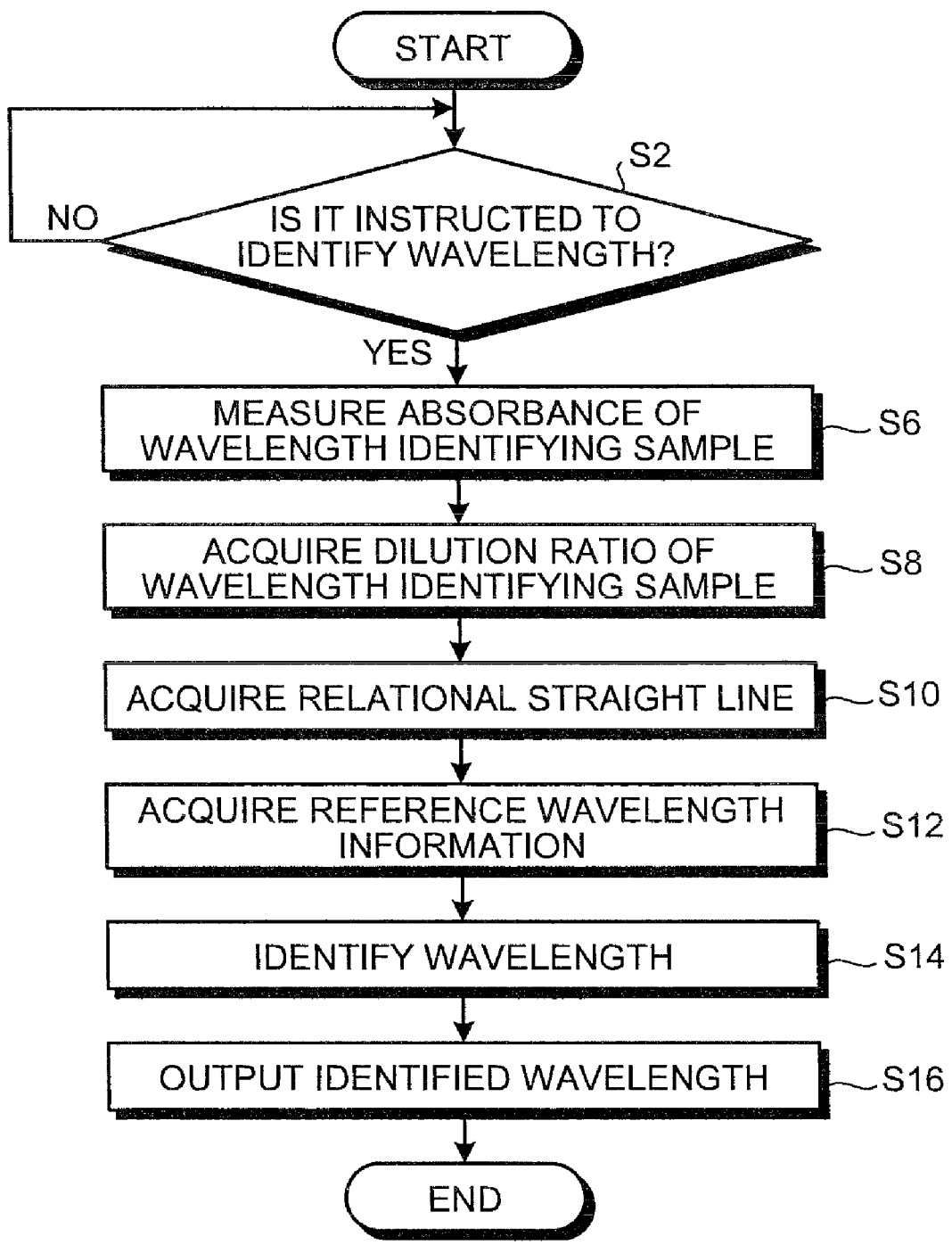

US 7,961,324 B2

WAVELENGTH IDENTIFICATION METHOD AND ANALYZER

CROSS-REFERENCE TO RELATED APPLICATIONS

This application is a continuation of PCT international application Ser. No. PCT/JP2007/072667 filed on Nov. 22, 2007 which designates the United States, incorporated herein by reference, and which claims the benefit of priority from Japanese Patent Application No. 2007-004896, filed on Jan. 12, 2007, incorporated herein by reference.

BACKGROUND OF THE INVENTION

1. Field of the Invention

The present invention relates to a wavelength identification method of identifying the actual wavelength of the light to be measured by the optical measuring system and an analyzer.

2. Description of the Related Art

Conventionally, as an apparatus that automatically analyzes specimen such as blood and body fluid, an analyzer that adds the specimen into a reaction vessel in which a reagent is dispensed, and optically detects the reaction occurred between the reagent and the specimen in the reaction vessel is known. In such an analyzer, after irradiating the reaction vessel containing the specimen with light, the analyzer analyzes the specimen based on the light intensity of a predetermined wavelength that has passed through the liquid contained in the reaction vessel.

To secure analysis accuracy of the analyzer, it is necessary for the analyzer to precisely identify the actual wavelength of the light to be measured by the analyzer, and to reflect the identified wavelength on the result of the measurement. Therefore, there has been proposed a method in which the light is transmitted through a correcting filter that transmits the light in such a way that the light has peaks at a plurality of predetermined wavelengths. Then the light that is transmitted through the correcting filter is received by array type light receiving elements, and based on which light receiving element has received each peak light, the actual wavelength of the light to be measured by the analyzer is identified (Refer to Japanese Patent Application Laid-Open No. H6-74823). Further, there has been proposed a method of confirming how much the current measuring wavelength has shifted from that of the time when the analyzer was manufactured, based on the difference between the current optical measurement result of the standard specimen of which measurement result is known and the optical measurement result of the standard specimen at the time when the analyzer was manufactured (Refer to Japanese Patent Application Laid-Open No. 2006-162355).

SUMMARY OF INVENTION

An analyzer according to an aspect of the present invention analyzes a sample based on the optical characteristics of the sample. The analyzer includes: a measuring unit that measures absorbances of two or more wavelength identifying samples having different concentrations and having absorbance characteristics in which there is no extremum in a wavelength band including a wavelength to be identified, the wavelength identifying samples being made of a same material; a calculator that obtains a gradient of a straight line indicating a relationship between the concentrations and the absorbances of the identifying samples measured by the measuring unit; and an identifier that identifies an actual wavelength of light to be measured by the measuring unit, based on a degree of coincidence between the gradient of the straight line calculated by the calculator and at least one pre-obtained reference gradient of a straight line indicating a relationship between concentrations and absorbances of reference samples made of the same material as the wavelength identifying samples for at least one wavelength.

A method according to another aspect of the present invention is for identifying an actual wavelength of light to be measured by an optical measuring system. The method includes: measuring absorbances of two or more wavelength identifying samples having different concentrations and having absorbance characteristics in which there is no extremum in a wavelength band including a wavelength to be identified, the wavelength identifying samples being made of a same material; calculating a gradient of a straight line indicating a relationship between the concentrations and the absorbances of the identifying samples measured in the measuring; and identifying the actual wavelength of the light to be measured by the optical measuring system, based on a degree of coincidence between the gradient of the straight line calculated in the calculating and at least one pre-obtained reference gradient of a straight line indicating a relationship between concentrations and absorbances of reference samples made of the same material as the wavelength identifying samples for at least one wavelength.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a flowchart illustrating a process procedure of the wavelength identifying process that is conducted in the analyzer illustrated in FIG. 1.

DETAILED DESCRIPTION OF THE PREFERRED EMBODIMENTS

Figure 1:
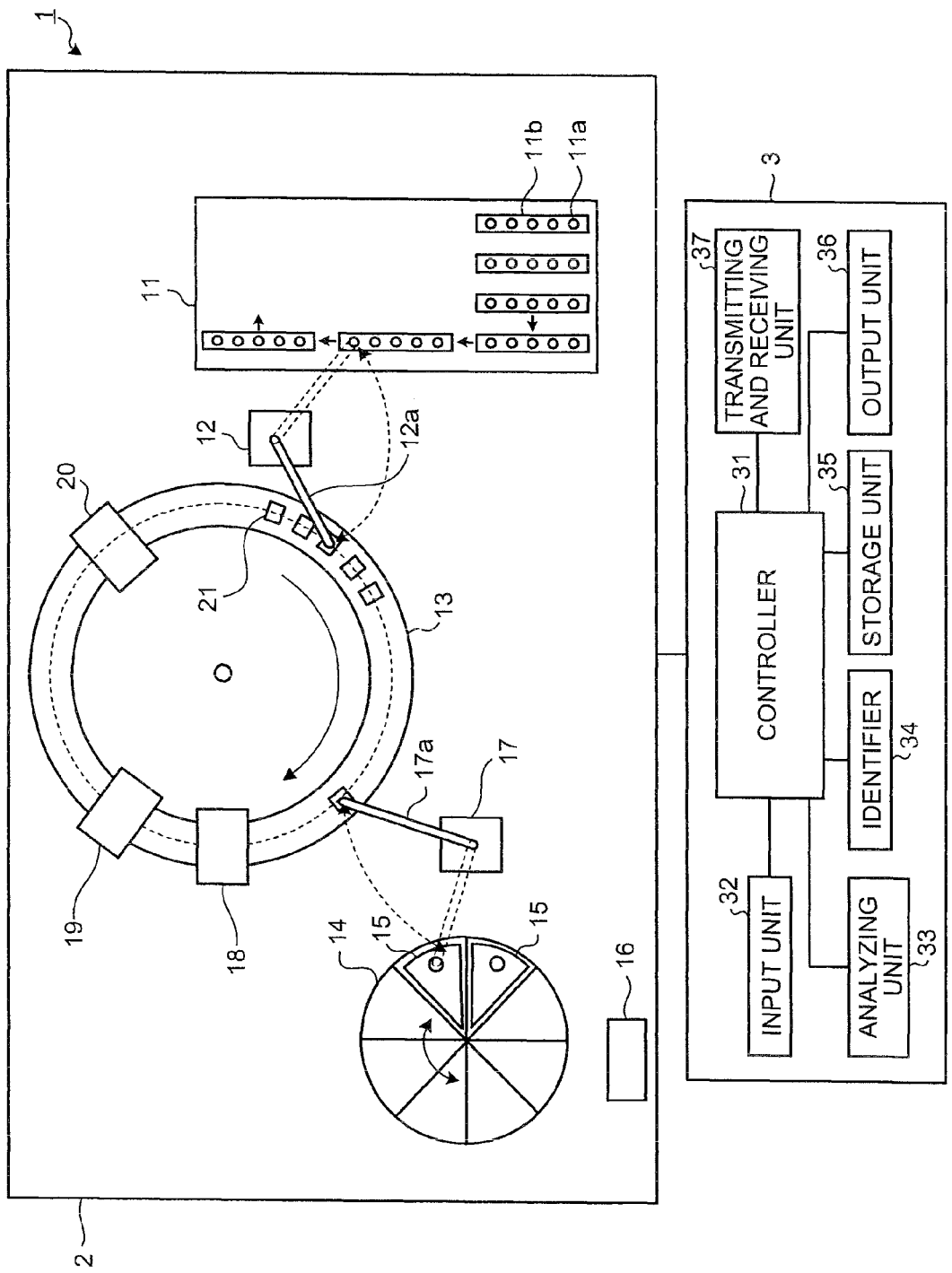
FIG. 1 is a schematic diagram illustrating a structure of a main portion of an analyzer according to an embodiment.

Referring to drawings, the wavelength identification method and the analyzer of the present embodiment are explained. In the present embodiment, the analyzer identifies the actual wavelength of the light to be measured by the optical measuring system. The present embodiment is explained taking an analyzer as an example, which analyzes the liquid specimen such as blood, urine, and the like based on the absorbance of the specimen. It is to be understood that the present invention is not limited to the present embodiment. In the drawings, the same reference numerals are given to the same parts.

FIG. 1 is a schematic diagram illustrating a structure of an analyzer 1 of the present embodiment. As illustrated in FIG. 1, the analyzer 1 includes: a measuring system 2 that dispenses the specimen as a target of the analysis and the reagent into each of reaction vessels 21, and optically measures the reaction that occurs in the reaction vessels 21; and a control system 3 that controls the overall operations of the analyzer 1 including the measuring system 2 and also analyzes the measuring result of the measuring unit 2. The analyzer 1 automatically conducts a biochemical analysis of a plurality of specimens as the two systems, the measuring system 2 and the control system 3, work together cooperatively.

Roughly classifying, the measuring system 2 includes, a specimen conveyor 11, a specimen dispensing system 12, a reaction table 13, a reagent storage 14, a reading unit 16, a reagent dispensing system 17, an agitator 18, an optical measuring unit 19, and a cleaning unit 20.

The specimen conveyor 11 includes a plurality of specimen racks 11b that holds a plurality of specimen vessels 11a containing liquid specimens such as blood and urine, and sequentially conveys the specimen racks 11b in the direction shown by arrows in the drawing. The specimen contained in the specimen vessels 11a that are conveyed to the predetermined position on the specimen conveyor 11 is dispensed, by the specimen dispensing system 12, into the reaction vessels 21 which are arranged and conveyed on the reaction table 13.

The specimen dispensing system 12 includes an arm 12a that ascends and descends in a vertical direction and freely rotates about a vertical line that passes through a proximal end portion thereof as a central axis. On the tip portion of the arm 12a, a probe that sucks and discharges the specimen is mounted. The specimen dispensing system 12 includes a not shown suck and discharge system that uses a suck and discharge syringe or a piezo element. With the probe, the specimen dispensing system 12 sucks the specimen from the specimen vessels 11a that are conveyed to the predetermined position of the specimen conveyor 11. Then the specimen dispensing system 12 swings the arm 12a in a clockwise direction in the drawing and dispenses the specimen into the reaction vessel 21 by discharging the specimen.

The reaction table 13 conveys the reaction vessel 21 to a predetermined position to dispense the specimen and reagent into the reaction vessel 21, to conduct agitating or cleaning of the reaction vessel 21, and to measurement the light. Under the control of a controller 31, as a not shown driving system is driven, the reaction table 13 is freely rotatable about a vertical line that passes through the center of the reaction table 13a as a rotational axis. The reaction table 13 is provided with a not shown freely openable and closeable lid and a constant-temperature bath on an upper side and lower side of the reaction table, respectively.

The reagent storage 14 is capable of storing a plurality of reagent vessels 15 in which the reagent that is to be dispensed into the reaction vessel 21 is contained. A plurality of storing cells is arranged at equal intervals in the reagent storage 14, and the reagent vessel 15 is detachably housed in each of the storing cells. Under the control of the controller 31 as the not shown driving system is driven, the reagent storage 14 is freely rotatable about a vertical line that passes through the center of the reagent storage 14 as a rotational axis in a clockwise or counterclockwise direction. The reagent storage 14 conveys a desired reagent vessel 15 to a position where the reagent dispensing system 17 sucks the reagent. The reagent storage 14 is provided with a freely openable and closeable lid (not shown) at the upper side thereof. A constant-temperature bath is provided at the lower side of the reagent storage 14. Thus, when the reagent vessel 15 is stored in the reagent storage 14 and the lid is closed, the reagent contained in the reagent vessel 15 is maintained in a constant-temperature-state, and evaporation and denaturing of the reagent contained in the reagent vessel 15 can be restrained.

A recording medium is placed on a side surface of the reagent vessel 15, and reagent information regarding the reagent contained in the reagent vessel 15 is recorded on the recording medium. The recording medium indicates coded various types of information that is read out optically. A reading unit 16 that optically reads out the recording medium is provided at a periphery portion of the reagent storage 14. The reading unit 16 emits infra-red ray or visual light toward the recording medium, processes the light reflected from the recording medium, and reads out the information recorded on the recording medium. The reading unit 16 may acquire information recorded on the recording medium by conducting image processing of the recording medium and by decoding the image information that is acquired by the image processing.

Like the specimen dispensing system 12, the reagent dispensing system 17 is provided with an arm 17a on which a probe that sucks and discharges the reagent is mounted at the tip portion thereof. The arm 17a ascends and descends in a vertical direction and freely rotates about a vertical line that passes through a proximal end portion thereof as a central axis. With the probe, the reagent dispensing system 17 sucks the reagent stored in the reagent vessel 15 that is conveyed to a predetermined position on the reagent storage 14. Then the reagent dispensing system 17 swings the arm 17a in a clockwise direction in the drawing and dispenses the reagent into the reaction vessel 21 that is conveyed to a predetermined position on the reaction table 13. The agitator 18 agitates the specimen and the reagent that is dispensed into the reaction vessel 21, and accelerates the reaction between the specimen and the reagent.

The optical measuring unit 19 irradiates the reaction vessel 21 conveyed to a predetermined optical measuring position with light. Then the optical measuring unit 19 spectroscopes the light that has passed through the liquid contained in the reaction vessel 21 and measures absorbance of the wavelength that is peculiar to the reaction liquid. The result of the measurement by the optical measuring unit 19 is output to the controller 31 and analyzed with an analyzing unit 33. The optical measuring unit 19 measures absorbances of two or more wavelength identifying samples having different concentrations and having absorbance characteristics in which there is no extremum in a wavelength band including a wavelength to be identified, the wavelength identifying samples being made of a same material.

With a not shown nozzle, the cleaning unit 20 sucks and discharges the mixed liquid in the reaction vessel 21 of which measurement with the optical measuring unit 19 is finished. Then, the cleaning unit 20 cleans the reaction vessel 21 by injecting and discharging cleaning fluid such as detergent, and rinse water, into and from the reaction vessel 21 with the not shown nozzle. The cleaned reaction vessel 21 is re-used, though the reaction vessel 21 may be discarded after a single measurement is finished depending on the contents of the examination.

The control system 3 is explained next. The control system 3 includes a controller 31, an input unit 32, an analyzing unit 33, an identifier 34, a storage unit 35, an output unit 36, and a transmitting and receiving unit 37. Each of the units included in the measuring system 2 and the control system 3 are electrically connected to the controller 31.

The controller 31 is constituted with CPU and the like, and controls processes and operations of each of the units of the analyzer 1. The controller 31 conducts a predetermined input/output control regarding the information that is input to or output from each of the components, and conducts predetermined information processing on the information.

The input unit 32 includes a keyboard, a mouse, and the like; and acquires various information that is necessary for the analysis of the specimen, and instructive information of analyzing operation and the like from outside. The analyzing unit 33 conducts componential analysis and the like of the specimen based on a result of absorbance measurement that is acquired from the optical measuring unit 19.

The identifier 34 identifies the actual wavelength of the light to be measured by the optical measuring unit 19. First, the identifier 34 calculates a gradient of a straight line that indicates a relationship between concentrations and absorbances of the wavelength identifying samples to be measured by the optical measuring unit 19. Then the identifier 34 identifies the actual wavelength of the light to be measured by the measuring unit by comparing a reference gradient(s) with the calculated gradient. The reference gradient(s) is a pre-obtained gradient(s) of a straight line(s) indicating a relationship between concentrations and absorbances of reference samples made of the same material as the wavelength identifying samples for one or more wavelengths. The reference gradients are obtained for the respective wavelengths to be identified. Each of the reference gradients is obtained based on the absorbances at the respective concentrations of the reference samples that are measured for the respective wavelengths by an optical measuring apparatus having higher optical reception sensitivity than the optical reception sensitivity of the optical measuring unit 19. The identifier 34 identifies the actual wavelength of the light to be measured by the optical measuring system based on a degree of coincidence between the reference gradient(s) and the calculated gradient. In the present embodiment, measuring process similar to the measuring process that is conducted on the ordinary specimen is conducted on two or more of the wavelength identifying samples having different concentrations. Then the actual wavelength of the light to be measured by the optical measuring unit 19 is identified based on the absorbances at the respective concentrations of the reference samples.

The storage unit 35 includes: a hard disk that magnetically stores therein information; and a memory that loads various programs relating to the process when the analyzer 1 conducts the process from the hard disk and electrically stores therein the programs. The storage unit 35 stores therein various kinds of information including the analysis result of the specimen and the like. The storage unit 35 stores therein the reference gradients that are pre-obtained for one or more wavelengths. The storage unit 35 may include an auxiliary storage device capable of reading out the information stored in recording media such as CD-ROM, DVD-ROM, PC card, and the like The output unit 36 includes a display, a printer, a speaker, and the like, and outputs various information including the analysis result of the specimen. The output unit 36 outputs the actual wavelength of the light, which has been identified by the identifier 34, to be measured by the optical measuring unit 19. The transmitting and receiving unit 37 has a function as an interface that conducts transmission and reception of the information that follows a predetermined format via a not shown communication network.

In the analyzer 1 structured in the aforementioned manner, the specimen dispensing system 12 dispenses the specimen contained in the specimen vessels 11a into the plurality of reaction vessels 21 that is sequentially conveyed in a row. After the reagent dispensing system 17 has dispensed the reagent contained in the reagent vessels 15 into the reaction vessels 21, the optical measuring unit 19 conducts spectrophotometric measurement of the sample which is in a state the specimen and the reagent are reacted. As the analyzing unit 33 analyzes the result of the spectrophotometric measurement, the componential analysis and the like of the specimen are automatically conducted. The reaction vessels 21 are conveyed after the measurement by the optical measuring unit 19 is finished. As the cleaning unit 20 cleans the reaction vessels 21 while the reaction vessels 21 are being conveyed, a series of analyzing operations is continuously and repeatedly conducted.

Figure 2:
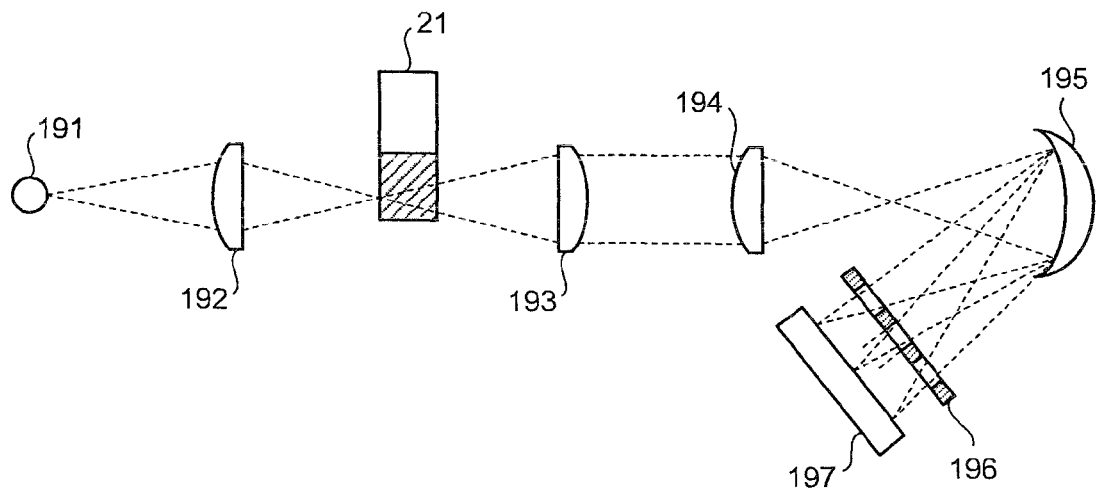
FIG. 2 is a schematic diagram illustrating a main portion of an optical measuring unit of FIG. 1.

Next, the optical measuring unit 19 illustrated in FIG. 1 is explained. As illustrated in FIG. 2, the optical measuring unit 19 includes: a light source 191 that radiates light; a lens 192 that collects the light radiated from the light source 191 toward the reaction vessel 21; lenses 193, and 194 that collect the light that has passed through the reaction vessel 21 toward the grating 195; a grating 195 that spectroscopes the light that is collected by the lenses 193, and 194; a slit member 196 that concentrates the light that is spectroscoped by the grating 195 on a wavelength-by-wavelength basis; and a photodiode array (hereinafter "PDA") 197 that receives light having their respective wavelengths that is spectroscoped by the grating 195. In the PDA 197, photodiodes (hereinafter "PDs") are one-dimensionally or two-dimensionally arranged. Each of the PDs detects an amount of the received light having the corresponding predetermined wavelength. Usually, in the analyzer that biochemically analyzes the specimens such as blood and urine, the light of 570 nm wavelength band is used as one of measuring lights. Therefore, in the present embodiment, a case as an example in which the wavelength of the light in 570 nm wavelength band is identified is explained, among the wavelengths that are received by the respective PDs of the PDA 197.

First, the wavelength identifying sample and the reference sample used for identifying the wavelength of the light of 570 nm band is explained. In the analyzer 1, the light of 570 nm band that is used by the optical measuring unit 19 includes some amount of error, shifting from the desired wavelength due to an adjustment error. For example, if the desired wavelength is 570 nm and there is an error range of 570 nm to 575 nm, in order to maintain high analysis accuracy, it is necessary to identify which wavelength of the light, among 570 nm to 575 nm, to be actually measured by the optical measuring unit 19.

Figure 3:
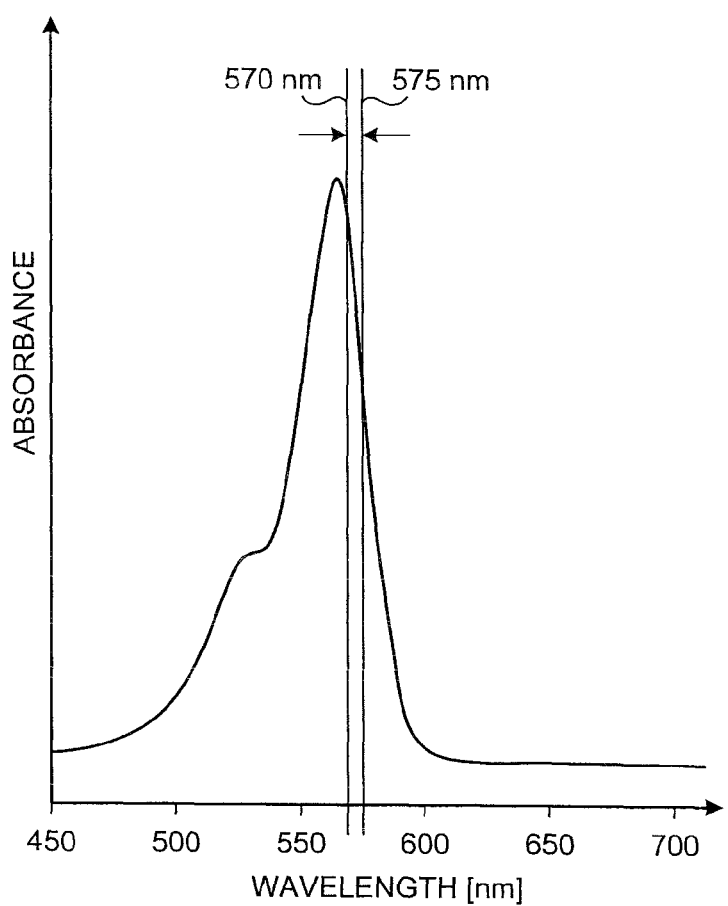
FIG. 3 is illustrates absorbance characteristic of Acid Red that is a wavelength identifying sample.

In the present embodiment, as illustrated in FIG. 3, as the wavelength identifying sample and the reference sample for identifying the wavelength of the light of 570 nm band, Acid Red that is the pigment solution is used. As illustrated in FIG. 3, Acid Red has absorbance characteristic in which there is no extremum and which has large derivative in the range of 570 nm to 575 nm that is the identifying target. Thus, in the range of 570 nm to 575 nm, Acid Red causes a great difference in the absorbance even if an absorption wavelength is changed by only 1 nm. As a result, by using the absorbances of Acid Red, it is possible to recognize the change of the wavelength of the light that is absorbed by Acid Red, by a unit of 1 nm or less. Acid Red has a high absorbance in the range of 570 nm to 575 nm, therefore, even if diluted; Acid Red can absorb the light of 570 nm to 575 nm wavelengths to a degree that the optical measuring unit 19 can measure the absorbance. Therefore, after diluting Acid Red to the respective concentrations, if the absorbances of the light of the respective wavelengths in the range of 570 nm to 575 nm are measured, the relationship between the concentrations and the absorbances for the respective wavelengths can be obtained. Meanwhile, the pigment solution which is used to identify the wavelength is recognized by the change of absorbance that corresponds to the change of absorbance-wavelength-change. Therefore, the pigment solution which is used to identify the wavelength is satisfactory if it has absorbance characteristics in which there is no extremum in the wavelength range that is a identifying target. Acid Red that is exemplarily shown in the present embodiment has absorbance characteristics having large derivative in the range of 570 nm to 575 nm that is the identifying target. Acid Red of the present embodiment causes a great difference in the absorbance by a minute change of the absorbance wavelength. As a result, it is possible to recognize the change of the wavelength of the light that Acid Red has absorbed by a minute unit.

Figures 4, 5:
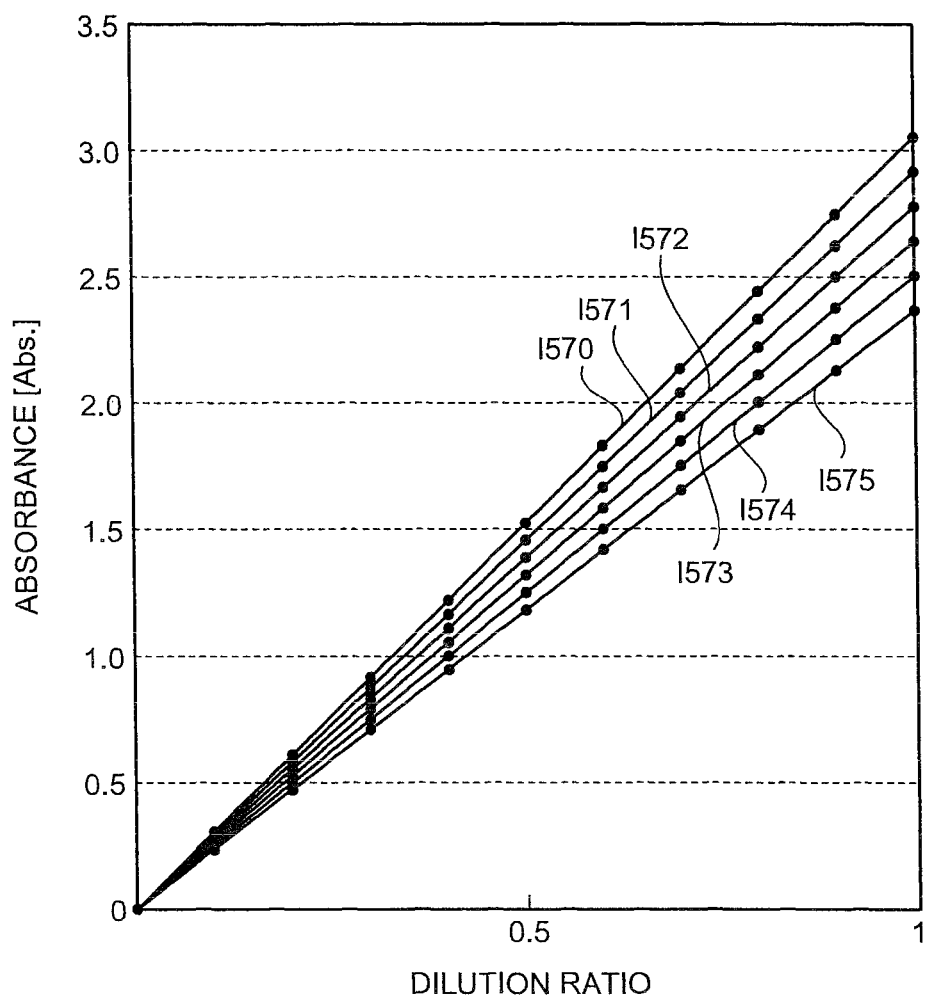
FIG. 4 illustrates measurement results of absorbances of Acid Red at respective concentrations measured by using light of 570 nm to 575 nm wavelength, Acid Red being obtained by diluting stock solution having a predetermined concentration at their respective dilution ratios.
FIG. 5 illustrates results of calculations of gradients "a" and intercepts "b" of straight lines corresponding to their respective wavelengths from 570 nm to 575 nm in FIG. 4.

FIG. 4 illustrates measurement results of the absorbances of Acid Red as the reference samples at the respective concentrations, which are actually measured with the light of wavelength of from 570 nm to 575 nm. Acid Red having the respective concentrations are obtained by diluting stock solution having a predetermined concentration at their respective dilution ratios. The measurement results illustrated in FIG. 4 correspond to the absorbances of Acid Red having 11 different concentration obtained by diluting stock solution having the predetermined concentration by changing the dilution ratio by 0.1, between 0 and 1. Then the absorbance of each of the wavelengths in the range of 570 nm to 575 nm is measured for each of the concentrations of Acid Red. As illustrated in FIG. 4, a relationship between the absorbances at the respective wavelengths of the light and the dilution ratios of Acid Red can be expressed by a linear function. In FIG. 4, a straight line 1570 indicates a relationship between the absorbances of 570 nm wavelength light and the respective dilution ratios of Acid Red; a straight line 1571 indicates a relationship between the absorbances of 571 nm wavelength light and the respective dilution ratios of Acid Red; a straight line 1572 indicates a relationship between the absorbances of 572 nm wavelength light and the respective dilution ratios of Acid Red; a straight line 1573 indicates a relationship between the absorbances of 573 nm wavelength light and the respective dilution ratios of Acid Red; a straight line 1574 indicates a relationship between the absorbances of 574 nm wavelength light and the respective dilution ratios of Acid Red; and a straight line 1575 indicates a relationship between the absorbances of 575 nm wavelength light and the respective dilution ratios of Acid Red. The absorbance of each concentration of Acid Red is measured with a spectrophotometer that has a narrower full-width at half-maximum of the reception wavelength than the full-width at half-maximum of the reception wavelength of the optical measuring unit 19, and the aforementioned spectrophotometer has higher light receiving sensitivity than the optical measuring unit has.

As illustrated by the straight lines 1570 to 1575 in FIG. 4, it is understood that the straight lines indicating the relationships between the absorbances of the light of the respective wavelengths of 570 nm to 575 nm and the respective dilution ratios of Acid Red have different gradients.

FIG. 5 illustrates results of calculation of gradients "a" and intercepts "b" of the straight lines corresponding to their respective wavelengths from 570 nm to 575 nm illustrated in FIG. 4. As illustrated in FIG. 5, the gradients "a" and the intercepts "b" of the straight lines corresponding to the respective wavelengths from 570 nm to 575 nm have different values depending on the respective wavelengths from 570 nm to 575 nm. The values of the gradient "a" corresponding to the respective wavelengths from 570 nm to 575 nm are based on the measurement results that are measured with the spectrophotometer having a higher light receiving sensitivity than that of the optical measuring unit 19 in the analyzer 1, therefore the values of the gradients "a" may presumably be treated as inherent to the respective wavelengths. The gradients "a" of the straight lines indicating the relationships between the respective dilution ratios of Acid Red as the reference samples and the absorbances corresponding to the respective wavelengths, illustrated in FIG. 5, are pre-obtained and stored in the storage unit 35.

The identifier 34 actually makes the optical measuring unit 19 measure the absorbances of Acid Red as the wavelength identifying samples at two or more diluting ratios. The identifier 34 calculates a gradient of a straight line that indicates a relationship between the dilution ratios of Acid Red and the absorbances measured by the optical measuring unit 19. Then the identifier 34 identifies the actual wavelength of the light to be measured by the optical measuring unit 19 by comparing the calculated gradient with the gradients "a" of the straight lines corresponding to the respective wavelengths illustrated in FIG. 5.

Figure 6:
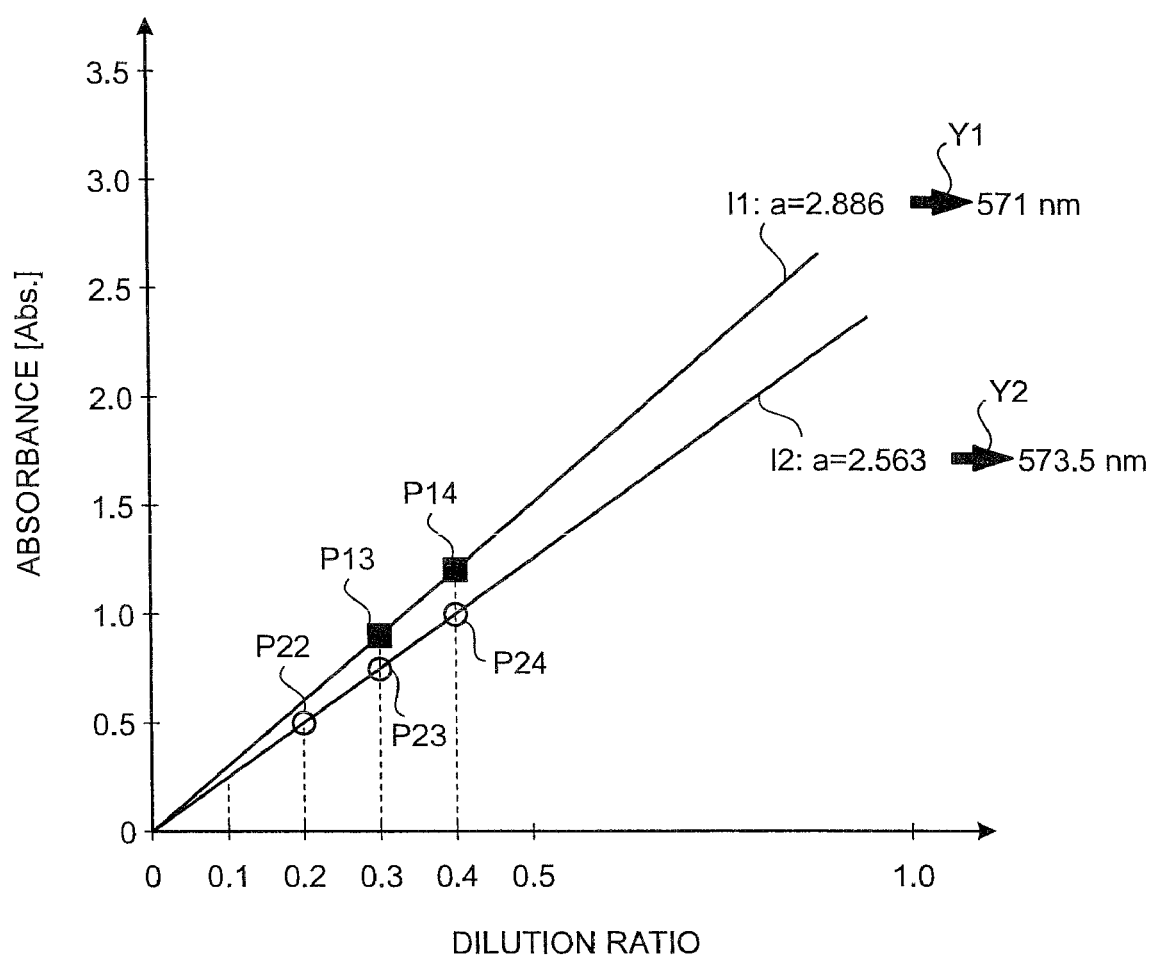
FIG. 6 is a drawing for explaining wavelength identifying process that is conducted in an identifying unit illustrated in FIG. 1.

Referring to FIG. 6, a content of process in which the identifier 34 identifies the wavelength is explained. For example, the case where the optical measuring unit 19 measures absorbances of Acid Red, as the wavelength identifying samples, of dilution ratios 0.3 and 0.4 is explained. In this case, the identifier 34 obtains a straight line 11 that passes through a point P13 and a point P14. The identifier 34 obtains the straight line 11 and calculates a gradient "a" of the straight line 11 based on the absorbance of Acid Red of dilution ratio 0.3 indicated by the point P13 and the absorbance of Acid Red of dilution ratio 0.4 indicated by the point P14 illustrated in FIG. 6. After calculating the gradient "a" of the straight line 11, the identifier 34 refers to the gradients of the respective wavelengths of the reference samples indicated in FIG. 5 that are stored in the storage unit 35, and then the identifier 34 determines the wavelength that coincides with the calculated gradient. In this case, the identifier 34 calculates the gradient "a" of the straight line 11 is 2.886, therefore as indicated by an arrow Y1, the identifier 34 determines the straight line 11 corresponds to the light whose wavelength is 571 nm, and then the identifier 34 identifies the actual wavelength of the light to be measured by the optical measuring unit 19 is 571 nm. Thus, in the analyzer 1, by using the gradients of the straight lines, inherent to the respective wavelengths, each indicating the relationship between the absorbances and the concentrations of the wavelength identifying samples and the reference samples, it is possible to accurately identify the actual wavelength of the light to be measured by the optical measuring unit 19.

Furthermore, a case where the optical measuring unit 19 measures absorbances of Acid Red, as the wavelength identifying samples, of dilution ratios of 0.2, 0.3, and 0.4 after a predetermined of time has elapsed are explained. In this case, the identifier 34 obtains a straight line 12 that passes through a point P22, a point P23, and a point P24. The identifier 34 obtains the straight line 12 and calculates a gradient "a" of the straight line 12 based on the absorbance of Acid Red of dilution ratio 0.2 indicated by the point P22, the absorbance of Acid Red of dilution ratio 0.3 indicated by the point P23, and the absorbance of Acid Red of dilution ratio 0.4 indicated by the point P24. After calculating the gradient "a" of the straight line 12, the identifier 34 refers to the gradients of the respective wavelengths of the reference samples indicated in FIG. 5 that are stored in the storage unit 35, and then the identifier 34 determines the wavelength that coincides with the calculated gradient "a". In this case, as the identifier 34 calculates the gradient "a" of the straight line 12 is 2.563, in FIG. 5, there is no gradient that coincides with that of the straight line 12. However, as the gradient of the straight line 12 is 2.563, the identifier 34 can determine the straight line 12 corresponds to the light whose wavelength is in the range of 573 nm to 574 nm because the values of gradients thereof are closest to the gradient "a" of the straight line 12.

By using the gradients of the wavelengths of 573 nm to 574 nm which are closest to the calculated gradient "a" of the straight line 12, the identifier 34 identifies a corresponding wavelength in detail by calculating a difference and ratio between the calculated gradient "a" of the straight line 12 and the gradients of the wavelengths of 573 nm to 574 nm. For example, the identifier 34 obtains a difference value between the calculated gradient "a" of the straight line 12 (2.563), and the gradient "a" of the wavelength 573 nm (2.6365). Subsequently, the identifier 34 obtains the difference value between the gradient "a" of the wavelength 573 nm (2.6365) which is closest to the calculated gradient "a" of the straight line 12 (2.563), and the gradient "a" of the wavelength 574 nm (2.4899). The identifier 34 calculates the ratio of the difference value between the gradient "a" of the wavelength 573 nm (2.6365) and the gradient "a" of the wavelength 574 nm (2.4899) against the difference value between the gradient "a" of the straight line 12 (2.563) and the gradient "a" of the wavelength 573 nm (2.6365). The identifier 34 can obtain the wavelength that corresponds to the straight line 12 by a unit of 0.1 nm, for example. When the straight line 12 of FIG. 6, the difference value between the gradient "a" of the straight line 12 (2.563) and the gradient "a" of the wavelength 573 nm (2.6365) accounts for 0.5 of the difference value between the gradient "a" of the wavelength 573 nm (2.6365) and the gradient "a" of the wavelength 574 nm (2.4899). Thus, based on the straight line 12, as an arrow Y2 indicates, the identifier 34 can identify the actual wavelength of the light to be measured by the optical measuring unit 19 is 573.5 nm. Thus it is possible to confirm that the actual wavelength of the light to be measured by the optical measuring unit 19 has shifted to the higher wavelength side by 2.5 nm from the previous measurement of the wavelength in which the straight line 11 corresponding to 571 nm is calculated. Thus in the analyzer 1, it is possible to unequivocally acquire the shift of the wavelength of the light to be measured by the optical measuring unit 19.

Next, referring to FIG. 7, the wavelength identifying process in the analyzer 1 is explained. As illustrated in FIG. 7, based on the instruction information input from the input unit 32, the identifier 34 determines whether or not the identifier 34 is instructed to identify the actual wavelength of the light to be measured by the optical measuring unit 19 (step S2). For example, when an operator operates the input unit 32 and selects a selection column for instructing the controller 31 to identify the wavelength, from menu columns displayed on a display screen which constitutes the output unit 36, an instruction-information for instructing the input unit 32 to identify the wavelength to be measured by the optical measuring unit 19 is input to the controller 31 from the input unit 32.

The identifier 34 repeats a determination at step S2 until it determines that it is instructed to identify the actual wavelength of the light to be measured by the optical measuring unit 19. If the identifier 34 determines that it is instructed to identify the wavelength of the light (S2: Yes), the identifier 34 instructs the optical measuring unit 19 to measure the absorbances of the wavelength identifying samples such as Acid Red diluted by the respective dilution ratios. Then the optical measuring unit 19 measures absorbances of the wavelength identifying samples (step S6) and outputs measurement results. Subsequently, based on information input from the input unit 32, the identifier 34 acquires the dilution ratios of the wavelength identifying samples that has been measured by the optical measuring unit 19 (step S8). Then the identifier 34 acquires a straight line that indicates a relationship between the dilution ratios of the wavelength identifying samples and the absorbances of the wavelength identifying samples (step S10), and calculates a gradient of the straight line. Then, as exemplarily illustrated in FIG. 5, the identifier 34 acquires the gradients of the respective straight lines each indicating the relationship between the dilution ratios and the absorbances of the identifying samples pre-obtained for one or more wavelengths. The identifier 34 acquires the aforementioned gradients of the respective straight lines of the reference samples as reference wavelength information from the storage unit 35 (step S12). Then, based on a degree of coincidence between the gradient of the straight line obtained at the step S10 and the gradients of the respective straight lines that are acquired as the reference wavelength information at the step S12, the identifier 34 identifies the actual wavelength of the light to be measured by the optical measuring unit 19 (step S14). The output unit 36 outputs the wavelength that has been identified by the identifier 34 (step S16). The operator confirms the identified wavelength output by the output unit 36, thereby recognizing the actual wavelength of the light to be measured by the optical measuring unit 19 of the analyzer 1. As a result the operator can conduct a corrective process of the optical measurement result more properly than before.

Thus, according to the present embodiment, by using the gradients of the straight lines, inherent to the respective wavelengths, each indicating the relationship between the absorbances and the concentrations of the wavelength identifying samples and the reference samples, it is possible to accurately identify the actual wavelength of the light to be measured by the optical measuring unit 19. Furthermore, in the present embodiment, the actual wavelength of the light to be measured by the optical measuring unit 19 is identified by conducting a measuring process for an exclusive sample for the wavelength identification. The measuring process conducted on the exclusive sample for the wavelength identification is similar to the measuring process that is applied to the ordinary specimen. According to the present embodiment, an exclusive unit for the wavelength identification that is conventionally needed is unnecessary, and there is no need to conduct cumbersome process that is different from the ordinary analyzing process. Therefore, it is possible to easily identify the actual wavelength of the light to be measured by the optical measuring unit 19.

In the wavelength identifying process by the identifier 34, the wavelength is identified by referring to FIG. 5. and using the gradients of the straight lines each indicating the relationship between the concentrations and the absorbances for a plurality of wavelengths. However the present invention is not limited to the above-described process. For example, the identifier 34 may refer to a gradient of a straight line that indicates a relationship between absorbances and concentrations for a single wavelength as a reference wavelength, and determine whether the gradient coincides with a gradient of a straight line that indicates a relationship between absorbances and concentrations of the wavelength identifying samples actually measured by the optical measuring unit 19. Then, the identifier 34 may simply identify whether the actual wavelength of the light to be measured by the optical measuring unit 19 coincides with or shifted from the reference wavelength. Moreover, in the present embodiment, using at least two identifying samples having different concentrations is sufficient to obtain the straight line that indicates the relationship between the absorbances and the concentrations of the wavelength identifying sample actually measured by the optical measuring unit 19.

In the present embodiment, it has been explained that the wavelength of the light of 570 nm band is identified by using Acid Red. The present invention is not limited to the present embodiment, but the wavelength may be identified by actually measuring absorbances of two or more samples having different concentrations and having absorbance characteristics in which there is no extremum in a desired wavelength range to be identified.

The analyzer 1, explained in the aforementioned embodiment, can be realized by executing a pre-prepared program on a computer system. The computer system realizes the process operation of the analyzer by reading out and executing the program stored in a predetermined recording medium. Here, the predetermined recording medium includes not only portable physical media such as flexible disk (FD), CD-ROM, MO disk, DVD disk, photo-magnetic disk, and IC card, but also includes all types of recording media that can be readable by the computer system, such as "communication media" that temporarily stores therein the program during transmission of the program, including a hard disk drive (HDD) provided inside or outside of the computer system. Moreover, the computer system acquires programs from control servers or other computer systems connected via a network, and executes the process operation of the analyzer by executing the acquired program.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer that analyzes a sample based on optical characteristics of the sample, comprising:
   a measuring unit that measures absorbances of two or more wavelength identifying samples having different concentrations and having absorbance characteristics in which there is no extremum in a wavelength band including a wavelength to be identified, the wavelength identifying samples being made of a same material;
   a calculator that obtains a gradient of a straight line indicating a relationship between the concentrations and the absorbances of the identifying samples measured by the measuring unit; and
   an identifier that identifies an actual wavelength of light to be measured by the measuring unit, based on a degree of coincidence between the gradient of the straight line calculated by the calculator and at least one pre-obtained reference gradient of a straight line indicating a relationship between concentrations and absorbances of reference samples made of the same material as the wavelength identifying samples for at least one wavelength,
   wherein the same material has an absorbance characteristic with a sufficiently large derivative in the wavelength band so as to accurately identify the actual wavelength of light to within 1 nm or less.

2. The analyzer according to claim 1, further comprising an output unit that outputs the actual wavelength of the light to be measured by the measuring unit, which has been identified by the identifier.

3. The analyzer according to claim 1, wherein the material of the identifying samples and the reference samples is pigment solution.

4. A wavelength identification method of identifying an actual wavelength of light to be measured by an optical measuring system, the method comprising:
   measuring absorbances of two or more wavelength identifying samples having different concentrations and having absorbance characteristics in which there is no extremum in a wavelength band including a wavelength to be identified, the wavelength identifying samples being made of a same material;
   calculating a gradient of a straight line indicating a relationship between the concentrations and the absorbances of the identifying samples measured in the measuring; and
   identifying the actual wavelength of the light to be measured by the optical measuring system, based on a degree of coincidence between the gradient of the straight line calculated in the calculating and at least one pre-obtained reference gradient of a straight line indicating a relationship between concentrations and absorbances of reference samples made of the same material as the wavelength identifying samples for at least one wavelength,
   wherein the same material has an absorbance characteristic with a sufficiently large derivative in the wavelength band so as to accurately identify the actual wavelength of light to within 1 nm or less.

5. The wavelength identification method according to claim 4, further comprising outputting the actual wavelength of the light to be measured by the optical measuring system, which has been identified in the identifying.

6. The wavelength identification method according to claim 4, wherein the material of the identifying samples and the reference samples is pigment solution.

* * * * *